(12) United States Patent
Lindekens et al.

(10) Patent No.: US 8,304,229 B2
(45) Date of Patent: Nov. 6, 2012

(54) SUBSTRATES, PREPARATION AND USE

(75) Inventors: Luc Lindekens, Merchtem (BE); Michel Tielemans, Wemmel (BE); Steven Cappelle, Roeselare (BE); Jose Remacle, Malonne (BE); Benoit De Becker, Forest (BE)

(73) Assignee: Cytec Surface Specialties, S.A., Drogenbos (BE)

( * ) Notice: Subject to any disclaimer, the term of this patent is extended or adjusted under 35 U.S.C. 154(b) by 1167 days.

(21) Appl. No.: 10/472,909

(22) PCT Filed: Mar. 20, 2002

(86) PCT No.: PCT/EP02/03102
§ 371 (c)(1),
(2), (4) Date: Sep. 25, 2003

(87) PCT Pub. No.: WO02/078835
PCT Pub. Date: Oct. 10, 2002

(65) Prior Publication Data
US 2004/0092006 A1 May 13, 2004

(30) Foreign Application Priority Data

Mar. 30, 2001 (EP) .................................... 01108134

(51) Int. Cl.
*C12M 3/00* (2006.01)
*C07H 21/04* (2006.01)
(52) U.S. Cl. ............... 435/288.4; 435/287.2; 435/287.9; 530/350; 436/23.1; 428/411.1
(58) Field of Classification Search ............... 435/288.4, 435/287.9, 287.2; 530/350; 536/23.1; 428/411.1
See application file for complete search history.

(56) References Cited

U.S. PATENT DOCUMENTS

| | | | |
|---|---|---|---|
| 4,138,299 A * | 2/1979 | Bolgiano ........................ 522/96 |
| 5,541,251 A | 7/1996 | Vandersmissen et al. |
| 5,662,887 A * | 9/1997 | Rozzi et al. ..................... 424/49 |
| 5,688,642 A | 11/1997 | Calvert et al. |
| 5,847,019 A * | 12/1998 | Conrad et al. .................... 522/2 |
| 6,156,478 A | 12/2000 | Liu et al. |
| 6,174,683 B1 | 1/2001 | Fagnani et al. |
| 6,780,980 B1 * | 8/2004 | Sigrist et al. .................. 536/18.5 |
| 6,878,399 B2 * | 4/2005 | Chabrecek et al. ............. 427/162 |
| 7,144,573 B2 * | 12/2006 | Guire et al. ................ 424/78.08 |
| 7,744,912 B1 * | 6/2010 | Hubbell et al. ................ 424/422 |
| 2004/0062911 A1 * | 4/2004 | Lauf et al. ...................... 428/138 |

FOREIGN PATENT DOCUMENTS

| | | |
|---|---|---|
| EP | 1 258 731 A2 | 11/2002 |
| WO | 01/01143 A2 | 1/2001 |
| WO | WO 01/16372 * | 3/2001 |
| WO | 01 01143 | 4/2001 |

OTHER PUBLICATIONS

Geysen et al. "Combinatorial Compound Libraries for Drug Discovery: An Ongoing Challenge" Nature Reviews, Mar. 2003, 2, 222-230.*
Zammatteo, Nathalie; *Comparison Between Different Strategies of Covalent Attachment of DNA to Glass Surfaces to Build DNA Microarrays*; Analytical Biochemistry; 280(1); (2000); pp. 143-150.
Beier et al., M; *Versatile Derivatisation of Solid Support Media for Covalent Bonding on DNA-Microchips*; Nucleic Acids Research; 27(9); (1999); pp. 1970-1977.

* cited by examiner

*Primary Examiner* — T. D. Wessendorf
(74) *Attorney, Agent, or Firm* — Wenderoth, Lind & Ponack, L.L.P.

(57) ABSTRACT

A process for preparing a substrate having thereon sites reactive with the reactive groups of a molecular probe, the process comprising the steps of applying to the substrate surface a material comprising one or more reactive sites having an activated ethylenically unsaturated double bond of the formula I:

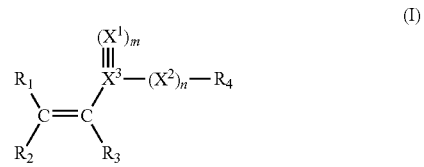

Figure 1:
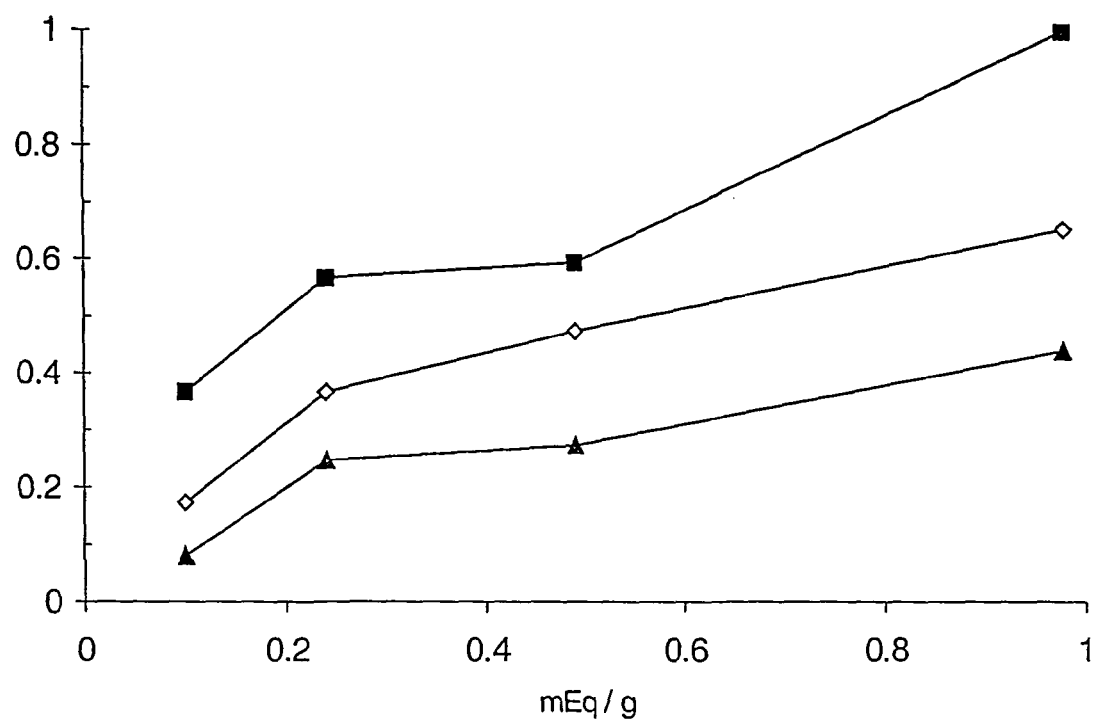

wherein the substituents are defined in the specification and, in a further step, covalently binding the reactive group of the molecular probe to the activated ethylenically unsaturated double bond of the reactive sites having formula I.

19 Claims, 1 Drawing Sheet

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Synthetic Construct

<400> SEQUENCE: 1
gaggaagctg cagaatggg                                                  19

<210> SEQ ID NO 2
<211> LENGTH: 27
<212> TYPE: DNA
<213> ORGANISM: Artificial Sequence
<220> FEATURE:
<223> OTHER INFORMATION: Synthetic Construct

<400> SEQUENCE: 2
ggtccttgtc ttatgtccag aatgctg                                         27
```

SUBSTRATES, PREPARATION AND USE

The present invention relates to improvements in reactive substrates, which can be used to form functionalised substrates having a probe bound thereto for use in multi-reactive systems, which for example interact with target molecules. Aspects of the invention relate to methods of chemically modifying the surface of a substrate for covalent binding of molecules thereon (such as molecular probes); substrates obtained and/or obtainable by said method; further methods for preparing a multi-reactive system using said substrate; a multi-reactive system obtained or obtainable by said methods; use of said multi-reactive systems in analysis and/or synthesis; products synthesised directly and/or indirectly using said multi-reactive systems; and/or use of information derived from said multi-reactive systems.

In embodiments herein the multi-reactive systems may be micro-arrays (e.g. DNA micro-arrays—also known as biochips); the probes may be DNA sequences and/or oligonucleotides and the information so derived may be (bio)chemical and/or biological information. Other uses of multi-reactive systems of the invention include high throughput screening.

A micro-array is an example of a multi-reactive system, which is a powerful tool that allows thousands of detection and analysis experiments to be run in parallel using tiny volumes of sample and reagents. Such massively parallel techniques are attractive to scientists when it is desired to run many experiments for example for screening purposes and/or to analyse and/or understand complex processes.

One such use is in the fields of DNA sequence identification and gene expression. Until DNA biochips became available, classical techniques based on the polymerase chain reaction (PCR) could only detect or study the expression of one gene at a time. Such techniques are described in "L'Avenir de la PCR: Diversification de Technologies et des Applications," Le Technoscope du Biofutur, 171, pp. 3-9 (1997) the disclosure of which is hereby incorporated by reference. In comparison, DNA chips allow analysis of up to hundreds of thousands of genes at once.

It will be appreciated that terms such as "multi-reactive systems", "micro-array"; "chip" and/or "biochip", are used herein to refer to system(s) and/or device(s) with the same or similar construction and/or underlying principles and are used herein interchangeably. Biochips refer to chips for use with biologically active molecules. DNA micro-array, DNA biochip, and DNA chip all refer to chips where the probes thereon are based on DNA sequences or oligonucleotides. Most examples herein refer to DNA chips and the prefix DNA may be omitted.

The underlying principle that makes possible a multi-reactive system such as a micro-array is the ability to selectively and durably bind various chemical species (such as a probe molecule) onto the surface of one or a series of substrate(s) optionally in a pattern thereon. Such substrates may be used in applications where the bound species can further interact with their environment whilst being firmly attached to the substrate. These substrates may also be used to measure and/or analyse (with suitable equipment) any given propert(ies) of interest for the entire series of species bound to the substrate (and/or series of substrates).

This is illustrated in more detail by the hybridisation process used by DNA-biochips. In this process a single-stranded DNA fragment binds preferentially to its complementary sequence when the two are in the presence of one another. The actual DNA biochip comprises a surface covered with an ordered array of up to several hundreds of thousands of single stranded DNA sequences also called capture probes; which could be oligonucleotides, cDNA or DNA fragments. Then the chip is exposed to a suspension of unknown, but labelled DNA sequences also called the target. The labelled targets will bind to their complementary sequence in a capture probe if it is present on the chip. Thus after careful cleaning, labels will be found only at positions where a fragment from the target sample has found its complementary capture probe. Since the sequence of each capture probe (and hence that of its complementary target) can be determined from its position, it is possible to gather information on the genetic content of the target sample.

DNA chips based on the preceding principle can be designed to serve many different uses. It is possible, for instance, to determine how gene expression varies as an individual is exposed to a given substance. Such experiments are of interest in the pharmaceutical industry to determine potential side effects of new drugs. DNA chips can also serve as diagnostic devices, for example to determine the exact strain of bacteria causing an infection so the most appropriate antibiotic is given to a patient. A DNA chip designed for such a use would prove much faster and more specific than any test currently used today. DNA micro-arrays can also help in the field of hereditary disease, where complex patterns of genes are differentiated sometimes by only a single base pair. In more fundamental research applications, micro-arrays will continue to be the tool of choice for work on gene sequencing and in other fields of biology for further understanding the complex processes governing cell life.

Hybridisation is only one type of interaction that can take place between molecules, so the concept of running thousands of parallel experiments can be applied to other areas. For instance, although DNA chips can give an insight as to what goes on in cells exposed to certain substances, certain information cannot be derived from studying gene expression. For example factors that occur at the mRNA or even the protein level complicate matters. Therefore protein chips used to identify and dose variations in protein level directly would also be of interest.

Other types of probes, which use non-biological molecules, are also of interest. For instance, to be used in high through-put screening a micro-array can be covered with selected active chemical substances whose various properties and/or various chemical and physical interactions with a sample can then be studied.

Presently there are two different methods to fabricate micro-arrays especially useful as DNA biochips, both of which have disadvantages.

One of the first methods used to make DNA chips was developed by Affymetrix and is based on the synthesis of all the molecules that will form the array in situ step by step (for example base by base for oligonucleotides). The techniques used are borrowed from the semiconductor manufacturing industry and use photolithography to selectively activate each location depending on whether the next base exposed to the micro-array does or does not fit that niche. Such techniques only allow probes of limited size to be used as for oligonucleotides and/or DNA longer than about 20 base pairs the combined errors introduced at each step of the manufacturing would make it difficult to arrive at reliable products. Moreover, this technique is cumbersome, time consuming, difficult to replicate in a regular laboratory setting, highly expensive and/or inflexible.

For non-DNA applications of micro-arrays moreover, photolithography is particularly unsuitable as photo-protective groups are often required to protect photo-liable groups on the chemical reagents and/or probes that are commonly used (which may comprise monomers). Preparing a diverse set of photo-protected building blocks would be impractical in an organic chemistry process.

The second method for preparing micro-arrays is the so-called delivery method that has recently gained in popularity. In the delivery method the probes or DNA fragments are directly grafted onto the substrate. They are first suspended in a suitable carrier medium, which is deposited as tiny droplets at the desired location(s) on the substrate by any suitable means. Typical droplet volumes are nano-litre ($1\times10^{-9}$ l) or even pico-litre ($1\times10^{-12}$ l) in volume. Suitable means for depositing the droplets comprise direct contact (for example micro-spotting) and/or ink-jet printing. However although depositing tiny droplets can be advantageous, to achieve a functional micro-array it is important that the substrate be prepared to ensure that the DNA probes will react therewith within the time it takes for a tiny droplet to evaporate (preferably by making a covalent bond). The delivery method is further described in detail in Micro-array Biochip Technology by Marc Schena published by Eaton Publishing (Natick, Mass., USA), 2000; the contents of which are hereby incorporated by reference.

Irrespective of the method used to prepare the micro-array, to function properly, it is important that the probes on the micro-arrays are sufficiently strongly attached to the micro-array substrate. Immobilised probes must not desorb during the different processing steps (such as the hybridisation, washing and/or analysis steps used with DNA biochips). To satisfy these requirements a covalent bond between the substrate and the probes is the preferred mode of attachment. Micro-arrays where the probes are strongly attached are advantageous as then the probe are more accessible to further processing steps (such as DNA hybridisation) hence improving the sensitivity of the micro-array.

For these reasons many attempts have been made to covalently bind probes to the substrate of a micro-array. For example, N. Zammateo et al. (Analytical Biochemistry, 280, pp. 143-15, 2000) have compared current techniques used for the particular case of glass substrates. Systems that were studied include phosphorylated DNA attached to aminated glass; aminated DNA attached to carboxylated glass; and aminated DNA attached to aldehyde-functional glass. The authors concluded that fixing aminated DNA to an aldehyde modified surface was the best coupling procedure to build DNA micro-arrays as measured by coupling yield and rate of reaction in the absence of coupling agent.

However the reaction of aldehyde-functional substrates with aminated probes, although effective, has the drawback of requiring an extra reduction step to stabilise the carbon-nitrogen bond that is formed. Although the initial reaction between an aldehyde group and a amino group forms a imine group (comprising a C=N double bond) which strongly attaches the probe to the surface, this reaction is reversible under many of the conditions experienced by micro-arrays in use. Therefore the imine group has to be reduced to an amine group (comprising the more resistant C—N single bond) in a further step to bind the probes covalently and more irreversibly to the substrate. A further problem is typical aldehyde functional groups are insufficiently stable on the substrate for prolonged storage and use. Thus aldehyde functionalised substrates require multiple processing steps and do not have the optimal balance between stability and reactivity required to graft the probes and provide a resistant substrate. Improved binding systems are still desired.

There remain many other problems with existing micro-arrays. It is difficult to obtain micro-arrays having an elevated functional and/or reactive site density and/or graft density. Yet it is desirable that micro-arrays should have as many probes as possible per unit area to improve the sensitivity of the micro-array. It is also important that the reactive sites and/or functionality on the substrate is obtained in a reproducible and adaptable way.

Without wishing to be bound by any mechanism it is believed that one means to solve some or all of the aforementioned problems may be to provide a functionalised substrate capable of reacting chemically with probes exposed thereto with sufficient speed so that a bond (preferably covalent bond) is formed between the probes and the substrate sufficiently quickly before the carrier medium in which the probes are applied has had time to dry. This problem is a particular issue where the probe is applied to the surface in tiny droplets of carrier medium as these very dry rapidly. Suitable substrates should react with the probes in a manner which is substantially irreversible under the conditions experienced by the substrate during use.

One further problem which may optionally be addressed by the present invention is to provide the correct combination between the chemistries of the probes (such as typical DNA probes used today) and those of the substrate, so it is possible to functionalise both of them. Still another optional problem to be solved by the present invention is to provide a functionalised and/or reactive substrate which remains stable under normal storage conditions, in the preliminary processing steps and/or in the environment preceding the binding of the probes. Thus it is not easy to find such a substrate which has the proper balance between high reactivity to the probes and stability during storage and use. Thus another optional object of the invention is to provide micro-arrays having a substrate with a surface to which the probes can be firmly attached by covalent bonds, and which is stable under the conditions of storage and use, both before and after the attachment of the probes. If such substrates are produced by known methods there are strict restrictions on the substrate materials that can be used as not all methods are compatible with all substrates. Most of the micro-arrays currently used are made of a glass substrate. Although glass has many advantageous properties, it has also drawbacks, for example, glass cannot be easily produced in any desired shape. Substrates having a wider variety of properties than glass are needed for developments such as an integrated lab-on-a-chip an d/or for use with microfluidic technologies. Polymers are the substrates of choice for such uses as they can be easily processed to form any desired shape, for example by moulding. Therefore optionally it is also desired to provide a method suitable for use with non-glass substrates as this would lead to improved micro-arrays. It is thus another optional object of the present invention to provide micro-arrays having some or all of advantages mentioned herein on a polymeric substrate.

Another optional object of the present invention provides micro-arrays where the density of the attached (optionally DNA) probes (i.e. graft density) is very high. It is also an optional object of the invention to provide substrates with an elevated graft density which is obtained in a reproducible way, and can be easily modified according to the needs of the user. Functionalised and/or reactive substrates may also be used with microfluidic systems and thus it is a further optional object of the invention to provide substrates suitable for such systems.

Accordingly it is an object of the broadest aspects of the present invention to address some or all of the preceding problems identified with prior art micro-arrays.

Therefore, according to the present invention, there is provided a process for preparing a substrate having thereon sites reactive with the reactive groups of a molecular probe, the process comprising the steps of applying to the substrate surface a material comprising one or more reactive sites having an activated ethylenically unsaturated double bond of the formula I:

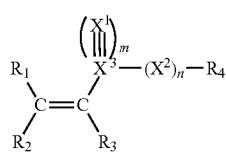

Formula 1

Wherein, if n=0, m=1, $X^3$ is carbon and $X^1$ is nitrogen, the bond between them being triple, and $R_4$ not exist;

if n=1, m=1, $X^3$ is carbon and $X^1$ is oxygen or sulphur, the bond between them being double, and $X^2$ is oxygen or sulphur or nitrogen substituted by an organo substituent;

if n=1, m=1 or 2, $X^3$ is sulphur and $X^1$ is oxygen, the bond between them being double, and $X^2$ is nitrogen substituted by an organo substituent;

$R_1$, $R_2$, each independently represent hydrogen, hydroxyl or organo group, $R_3$ and $R_4$ each independently represent hydrogen or organo group, eventually containing a silicon atom, $R_1$ and $R_2$ being not linked to $R_4$.

and, in a further step, of covalently bound the reactive group of the molecular probe to the activated ethylenically unsaturated double bond of the reactive sites having formula I.

According to the invention, the linking reaction between the reactive sites located onto the substrate and the molecular probe has at least one of following characteristics:

(i) the linking reaction is sufficiently fast so that the reaction is substantially complete under the process conditions used;

(ii) the reaction form a strong link between the species and the substrate in a single step; and/or (iii) the linking between the species and the substrate is substantially irreversible under the conditions of use of the substrate.

A "reactive substrate" as used herein denotes a substrate having an effective concentration of free reactive sites of formula I deposed on the surface thereof.

Optionally the substrates are suitable for use in a multi-reactive system such as a micro-array.

As used herein the molecular probe denotes a probe such as a biomolecule such as DNA, RNA, proteins, biotins, toxins, herbicides, pesticides, carbohydrates, drug targets, antibiotics, cell poisons, steroids, peptides, nucleotides, peptides nucleic acids, binding partners, haptenes, etc. In an embodiment of the invention, the final probe used in the multi-reactive system may comprise one or more various other species attached in successive fashion (e.g. in a chain) to the first probe bound to the reactive site on the substrate. In this manner probes with any desired property can be used even if they are not suitable (and/or cannot be modified to be so) for directly linking to the reactive sites on the substrate.

Optionally the carrier medium is a fluid, such as a liquid in which the molecular probe may be dispersed.

Preferably the fluid and/or species is applied in the form of droplets, more preferably by means of a directed method such as micro-spotting and/or inkjet printing (such as thermal and/or piezo ink-jet printing e.g. piezo) with for example an average droplet volume of one nano-litre or less.

Optionally the linking reaction occurs in a sufficiently fast manner that the reaction is substantially complete before the carrier fluid has evaporated therefrom (for example where the carrier fluid is applied as droplets).

The terms "strongly linked" and/or "strongly attached" as used herein mean substantially resistant to removal under the conditions (and with the other reagents) under which the micro-arrays and/or substrates will be used. Preferably this means that the molecular probe is linked to the reactive site by a covalent bond; more preferably via an average of at least one covalent bond per reactive site to probe link. More preferably the bond so formed is substantially irreversible under the conditions of use of the micro-array and/or is formed by a reaction which is substantially irreversible. Preferred covalent bonds are carbon to carbon bonds and/or carbon to nitrogen bonds and are more preferably saturated bonds, for example a C—N single bond.

The reactive sites may be intrinsic to the substrate surface itself in which case no pre-treatment may be required to use the substrate in the process of the invention. Alternatively, or as well, reactive sites may be added in the form of another material comprising such reactive sites and which is added on the substrate e.g. as a coating. The advantage of using a material with reactive sites is that this allows a much wider variety for choice of the underlying supporting substrate.

Therefore preferably the process further comprises the step of applying and fixing a material to the substrate, the material comprising reactive sites. More preferably the material is a coating composition and/or a gel. Preferably the material is polymerisable and there is a step of polymerising the material in situ on the substrate to form a coating thereon. More preferably said coating comprises reactive sites which have survived the polymerisation process, most preferably in sufficient concentration to strongly link a molecular probe thereto sufficient for use in a multi-reactive system such as a micro-array.

The invention also comprises those substrates suitable for being treated in the process of the invention, such substrates comprising those having intrinsically reactive sites thereon and/or those comprising a material thereon which comprises the reactive sites.

It will also be appreciated that as used herein substrate denotes any suitable support and may comprise any suitable material capable of supporting the species bound thereto as described herein and may be of any suitable shape such as flat, roughed and/or curved. Such supports can be membranes, microwels, multiwell plates, centrifuge tubes, films, microscope slides for example.

Substrates of the invention can be two dimensional such a the surface of substantially planar self supporting sheet. However other suitable non-planar substrates may also be used such as those comprising 2-D exterior surfaces and/or parts thereof upon any article of suitable material.

The substrate may also be three dimensional where the surface should be considered any exposed surface whether at the exterior and/or within the interior voids of an article and/or part thereof, for example articles of porous material and/or with porous coatings thereon (such as sintered glass) The porosity should be such that the article can be readily impregnated with a suitable carrier composition as described herein to functionalise the exposed surfaces thereof (including those in the voids and/or interstices). Other 3-D substrates that may be used comprise materials (either as the substrate per se and/or as a coating thereon) in a physical form which is highly open and/or of a high surface area such as dispersions having a gas as the dispersed phase e.g. hydrogels and/or aerogels. For 3-D substrates it is preferred that instead of units of exterior area the graft density should be measured per unit volume or per unit surface area (as measured by any suitable technique such as desorption).

The desired parallelism as described herein may be achieved in many ways. The term multi-reactive system as used herein broadly denotes any system that provides a series of many reactive sites which may be treated in parallel and for example can be used to perform large numbers of often chemically similar reactions at the same time (e.g. massively parallel systems). Thus broadly a multi-reactive system encompasses at least two different types of system as described below. As used herein it will be understood that in the broadest aspects of the invention the term "micro-array" may be substituted by the term "multi-reactive system" where appropriate. Broadly the same preparation techniques and chemistries (such as those described herein with reference to micro-arrays of the invention) can be used for any multi-reactive system of the invention with any necessary modifications which will be understood to those skilled in the art.

A first type of multi-reactive system of the invention comprises a functionalised substrate as part of a single device such as a micro-array which for example comprises a large number of separate but co-joined and/or contiguous sites thereon (which may be multifunctional, and/or heterogeneously functionalised and/or patterned thereon). Information may be derived about the properties of a site from its location in the pattern e.g. in an array. A specific example of a system of this type is a flat planar sheet (such as a glass or polymer slide) comprising on its surface a grid of different sites having probes fixed thereon in a pre-arranged pattern. The target species can then be exposed to the whole grid.

Multi-reactive systems of the invention can also comprise a second type in which the system comprises and/or is formed from a series of many (preferably small or micro-sized) functionalised substrates (optionally non-planar surface-functionalised species) each of which (and/or of groups of which) may react differently to the environment due to the nature of the reactive site and/or probe and/or specific combination(s) and/or mixture(s) thereof. For example each substrate may comprise only one type of site and probe fixed thereon (homogeneously reactive) although each (or each group of) substrate(s) is different. Information may derived from statistical analysis and/or isolating species having selected properties (e.g. the number and/or distribution of species having certain properties can be measured and/or certain can be collected). Such substrate mixtures can be formed together by being prepared in situ and/or may comprise a plurality of separately prepared substrates which are subsequently mixed together in the desired proportions before use.

Thus the usefulness of multi-reactive systems is that they comprise multiple components which interact differentially to their environment and thus allow a multitude of experiments to be performed substantially simultaneously (in parallel). As described above this may be achieved by two types of system, exemplified by micro-arrays having different properties at defined locations thereon and/or by a population of functionalised species each uniformly functionalised thereon but each having different properties.

Micro-arrays may be prepared from a material (such as coating or gel) comprising and/or applied to the surface of a substrate, said material comprising reactive sites. An organic probe comprising chemical groups reactive with said reactive sites may thereafter be strongly linked (preferably covalently linked) with said material by means of a suitable reaction. Preferably the material is polymerised in situ on the substrate to which it is attached (or which it forms) such that after polymerisation sufficient reactive sites remain to strongly link the organic probe thereto. It is also possible that the material comprises molecules comprising said reactive sites. The material may also be grafted onto the substrate and/or may form part of the substrate surface (i.e. the substrate inherently comprises the reactive sites without the need for further coating).

It is also possible to have reactive sites on the substrate which are capable of reacting with a polyfunctional (preferably di-functional) linking species to form another reactive site at the same location which may be the same as or different from the first. For example an hydroxy functional site on the substrate may react with an isocyanate group on an isocyanato (meth)acrylate to give a new reactive site with a free (meth)acrylate moiety thereon linked to the surface of the substrate through the linking urethane (meth)acrylate. Substrates functionalised in this manner also comprise the present invention and may also be used as described herein.

Advantageously the substrate is first coated with a polymerisable composition containing an activated unsaturated moiety. The coating is polymerised in a second step, in such a manner that the activated unsaturated moiety remains on the coating. In a third step, the coated substrate is made to react with an organic probe comprising groups reactive with the activated ethylenically unsaturated double bond in an addition reaction.

A still other aspect of the present invention provides a multi-reactive system comprising one or more functionalised substrates as described herein having molecular probes deposed thereon.

A yet further aspect of the present invention provides a process for using a multi-reactive system the process comprising the step of applying to one or more functionalised substrate(s) of the invention as described herein, target molecules, optionally dispersed in one or more carrier media.

The target may be used to provide information about the target and/or the medium from which it came and/or environment to which the multi-reactive system is and/or has been exposed.

Preferably where the multi-reactive system comprises a single substrate (such as micro-array) the activated unsaturated moiet(ies) and/or complement(s) thereof are deposited thereon in a pre-selected pattern such as a 2-D grid.

The multi-reactive system (such as micro-arrays) obtained and/or obtainable as described herein may be used to determine information (such as structure, concentration and/or any other useful chemical, biochemical and/or biological information) about organic molecules complementary to those strongly linked to the substrate as described herein. The micro-array(s) may also be used to bind preferentially to one or more selected species in a liquid to which the micro-array is exposed. This could be useful for example where it is desired to inactivate or target biologically active species (e.g. if the probe comprises a biologically active anti-body).

Other non limiting embodiments of the invention (besides those mentioned elsewhere herein) comprises use of the substrates and/or multi-reactive systems of the invention in any and/or all of the following fields of use including any possible combinations thereof:

The substrate of the invention is used in applications like cDNA and oligonucleotide chips, biochemical immunoassays, proteonomics, gene expression, drug target identification, pharmacogenomics, drug/toxin activity predection, discovery of therapeutic targets and improved medical treatment, biological sample analysis, proteins-proteins interactions, screening of chemical entities for proteins drug targets.

Other applications is detection and/or assay (for presence and/or concentration) of: impurities, contaminants, reaction by-products, micro-flora; micro-fauna, pathogens and/or undesirable ingredients. For example in foodstuffs it can be desirable to detect substances such as genetically modified material, antibiotics and/or hormones in for example milk or meat. Thus the invention can be used to provide improved quality control and/or labelling of ingredients in products.

Still other applications are detection and/or tests useful for biological, pharmaceutical and/or veterinarian conditions in animals and/or humans such diseases and/or disorders; and/or to provide diagnostic tools, treatments, therapies and/or prophylaxis therefor; and/or for any other pharmaceutical and/or veterinarian use, such as DNA-RNA and/or RNA-peptide interaction studies.

Another aspect of the present invention may provide a method of preparing substrates in which a substrate may be coated with a polymerisable composition containing one or more activated unsaturated moiet(ies); the coating may then be polymerised in a manner so the activated unsaturated moiet(ies) remain on the coating; and in an further step, the coated substrate may then react with an organic probe comprising groups reactive with the activated unsaturated moiety in an addition reaction.

Yet other aspect of the present invention may provide a method of preparing micro-arrays in which a coating composition may be deposited on the surface of a substrate; may then be polymerised in situ to form a coating thereon comprising activated unsaturated moiet(ies) after the polymerisation; and thereafter an organic probe comprising chemical group(s) reactive with the activated unsaturated moiet(ies) may be covalently bound thereto by means of an addition reaction.

A further aspect of the present invention may provide a substrate comprising organic probes strongly linked to the surface thereof through an activated unsaturated addition reaction, the organic probes being arranged and/or deposed thereon in a pattern and/or micro-array. Throughout this specification, the term "activated unsaturated moiety" "is used to denote a species comprising at least one unsaturated carbon to carbon double bond in chemical proximity to at least one activating moiety. This species is represented by formula I. Preferably the activating moiety comprises any group which activates an ethylenically unsaturated double bond for addition thereon by a suitable electrophillic group. Conveniently the activating moiety comprises oxy, thio, (optionally organo substituted)amino, thiocarbonyl and/or carbonyl groups (the latter two groups optionally substituted by thio, oxy or (optionally organo substituted) amino). They also comprise sulfonamides, sulfones and sulfoxide groups. More convenient activating moieties are (thio)ether, (thio)ester and/or (thio)amide moiet(ies). Most convenient "activated unsaturated moieties" comprise an "unsaturated ester moiety" which denotes an organo species comprising one or more "hydrocarbylidenyl(thio)carbonyl(thio)oxy" and/or one or more "hydrocarbylidenyl(thio)-carbonyl(organo)amino" groups and/or analogous and/or derived moieties for example moieties comprising (meth)acrylate functionalities and/or derivatives thereof. "Unsaturated ester moieties" may optionally comprise optionally substituted generic α,β-unsaturated acids, esters and/or other derivatives thereof including thio derivatives and analogs thereof.

The activated unsaturated moieties are those represented by Formula 1.

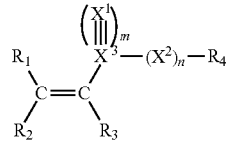

Formula 1

Where
if n=0, m=1, $X^3$ is carbon and $X^1$ is nitrogen, the bond between them being triple, and R does not exist;
if n=1, m=1, $X^3$ is carbon and $X^1$ is oxygen or sulphur, the bond between them being double, and $X^2$ is oxygen or sulphur or nitrogen substituted by an organo substituent;
if n=1, $X^3$ is carbon and $X^1$ is oxygen or sulphur, the bond between them being double, and $X^2$ is oxygen or sulphur or nitrogen substituted by an organo substituent;
if n=1, m=1 or 2, $X^1$ is sulphur and $X^1$ is oxygen, the bond between them being double, and $X^2$ is nitrogen substituted by an organo substituent;
$R_1$, $R_2$, each independently represent hydrogen, hydroxyl or organo group, $R_3$ and $R_4$ each independently represent hydrogen or organo group, eventually containing a silicon atom, $R_1$ and $R_2$ being not linked to $R_4$.

It will be appreciated that the Formula 1 herein may represent a discrete chemical species (such as a compound, ion, free radical, oligomer and/or polymer) and/or any part(s) thereof. Thus Formula 1 may also represent multivalent (preferably divalent) radicals. Thus the options given herein for $R_1$, $R_2$, $R_3$, $R_4$ and $R_5$ also encompass corresponding bi or multivalent radicals as appropriate.

More preferred moieties of Formula 1 (including isomers and mixtures thereof) are those where n is 1; $X^1$ is O; $X^2$ is O, S or $NR_5$; $X^3$ is carbon.

$R_1$, $R_2$, $R_3$, and $R_4$ are independently selected from: H, optional substituents and optionally substituted $C_{1-10}$hydrocarbo, and where present $R_5$ is selected from H and optionally substituted $C_{1-10}$hydrocarbo.

Most preferably n is 1, $X^1$ is O; $X^2$ is O or S, $X^3$ is carbon and $R_1$, $R_2$, $R_3$ and $R_4$ are independently H, hydroxy and/or optionally substituted $C_{1-6}$hydrocarbyl. $R_4$ may also represent a $C_{1-6}$ hydrocarbylalkoxy silane.

For example n is 1, $X^1$ and $X^2$ are both O; and $R_1$, $R_2$, $R_3$ and $R_4$ are independently H, OH, and/or $C_{1-4}$alkyl or $R_4$ is a $C_{1-4}$alkylsilane.

For moieties of Formula 1 where n is 1 and $X^1$ and $X^2$ are both O and $X^3$ is carbon, then: When one of ($R_1$ and $R_2$) is H and also $R_3$ is H, Formula 1 represents an acrylate moiety, which includes acrylates (when both $R_1$ and $R_2$ are H) and derivatives thereof (when either $R_1$ or $R_2$ is not H). Similarly when one of ($R_1$ and $R_2$) is H and also $R_3$ is $CH_3$, Formula 1 represents an methacrylate moiety, which includes methacrylates (when both $R_1$ and $R_2$ are H) and derivatives thereof (when either $R_1$ or $R_2$ is not H). Acrylate and/or methacrylate moieties of Formula 1 are particularly preferred.

Conveniently moieties of Formula 1 are those where n=1; $X^1$ & $X^2$=O; $X^3$ is carbon; $R_1$ and $R_2$ are independently H, methyl or OH, and $R_3$ is H or $CH_3$.

More conveniently moieties of Formula 1 are those where n=1; $X^1$ & $X^2$=O; X3 is carbon; $R_1$ is OH, $R_2$ is $CH_3$, and $R_3$ is H, and/or tautomer(s) thereof (for example of an acetoacetoxy functional species).

Most convenient unsaturated ester moieties are selected from: —OCO—CH=CH$_2$; —OCO—C(CH$_3$)=CH$_2$; acetoacetoxy, —OCOCH=C(CH$_3$)(OH) and all suitable tautomer(s) thereof. It will be appreciated that any suitable moieties represented by Formula 1 could be used in the context of this invention such as other reactive moieties.

The terms 'optional substituent' and/or 'optionally substituted' as used herein (unless followed by a list of other substituents) signifies the one or more of following groups (or substitution by these groups): carboxy, sulpho, formyl, hydroxy, amino, imino, nitrilo, mercapto, cyano, nitro, methyl, methoxy and/or combinations thereof. These optional groups include all chemically possible combinations in the same moiety of a plurality (preferably two) of the aforementioned groups (e.g. amino and sulphonyl if directly attached to each other represent a sulphamoyl radical). Preferred optional substituents comprise: carboxy, sulpho, hydroxy, amino, mercapto, cyano, methyl and/or methoxy.

The terms 'organic substituent' and "organic group" as used herein (also abbreviated herein to "organo") denote any univalent or multivalent moiety (optionally attached to one or more other moieties) which comprises one or more carbon atoms and optionally one or more other heteroatoms. Organic groups may comprise organoheteryl groups (also known as organoelement groups) which comprise univalent groups containing carbon, which are thus organic, but which have their free valence at an atom other than carbon (for example organothio groups). Organic groups may alternatively or additionally comprise organyl groups which comprise any organic substituent group, regardless of functional type, having one free valence at a carbon atom. Organic groups may also comprise heterocyclic groups which comprise univalent groups formed by removing a hydrogen atom from any ring atom of a heterocyclic compound: (a cyclic compound having as ring members atoms of at least two different elements, in this case one being carbon). Preferably the non carbon atoms in an organic group herein may be selected from: hydrogen, phosphorus, nitrogen, oxygen silicon and/or sulphur, more preferably from hydrogen, nitrogen, oxygen, phosphorous and/or silicon.

Most preferred organic groups comprise one or more of the following carbon containing moieties: alkyl, alkoxy, alkanoyl, carboxy, carbonyl, formyl and/or combinations thereof; optionally in combination with one or more of the following heteroatom containing moieties: oxy, thio, sulphinyl, sulphonyl, amino, imino, nitrilo and/or combinations thereof. Organic groups include all chemically possible combinations in the same moiety of a plurality (preferably two) of the aforementioned carbon containing and/or heteroatom moieties (e.g. alkoxy and carbonyl if directly attached to each other represent an alkoxycarbonyl group). The term 'hydrocarbo group' as used herein is a sub-set of a organic group and denotes any univalent or multivalent moiety (optionally attached to one or more other moieties) which consists of one or more hydrogen atoms and one or more carbon atoms and may comprise saturated, unsaturated and/or aromatic moieties. Hydrocarbo groups may comprise one or more of the following groups. Hydrocarbyl groups comprise univalent groups formed by removing a hydrogen atom from a hydrocarbon. Hydrocarbylene groups comprise divalent groups formed by removing two hydrogen atoms from a hydrocarbon the free valencies of which are not engaged in a double bond. Hydrocarbylidene groups comprise divalent groups (represented by "R$_2$C="") formed by removing two hydrogen atoms from the same carbon atom of a hydrocarbon, the free valencies of which are engaged in a double bond. Hydrocarbylidyne groups comprise trivalent groups (represented by "RC≡"), formed by removing three hydrogen atoms from the same carbon atom of a hydrocarbon the free valencies of which are engaged in a triple bond. Hydrocarbo groups may also comprise saturated carbon to carbon single bonds; unsaturated double and/or triple carbon to carbon bonds (e.g. alkenyl, and/or alkynyl groups respectively) and/or aromatic groups (e.g. aryl) and where indicated may be substituted with other functional groups.

The term 'alkyl' or its equivalent (e.g. 'alk') as used herein may be readily replaced, where appropriate and unless the context clearly indicates otherwise, by terms encompassing any other hydrocarbo group such as those described herein (e.g. comprising double bonds, triple bonds, aromatic moieties (such as respectively alkenyl, alkynyl and/or aryl) and/or combinations thereof (e.g. aralkyl) as well as any multivalent hydrocarbo species linking two or more moieties (such as bivalent hydrocarbylene radicals e.g. alkylene).

Any radical group or moiety mentioned herein (e.g. as a substituent) may be a multivalent or a monovalent radical unless otherwise stated or the context clearly indicates otherwise (e.g. a bivalent hydrocarbylene moiety linking two other moieties). However where indicated herein such monovalent or multivalent groups may still also comprise optional substituents. A group which comprises a chain of three or more atoms signifies a group in which the chain wholly or in part may be linear, branched and/or form a ring (including spiro and/or fused rings). The total number of certain atoms is specified for certain substituents for example $C_{1-N}$organo, signifies a organo moiety comprising from 1 to N carbon atoms. In any of the formulae herein if one or more substituents are not indicated as attached to any particular atom in a moiety (e.g. on a particular position along a chain and/or ring) the substituent may replace any H and/or may be located at any available position on the moiety which is chemically suitable or effective.

Preferably any of the organo groups listed herein comprise from 1 to 36 carbon atoms, more preferably from 1 to 18. It is particularly preferred that the number of carbon atoms in an organo group is from 1 to 10, especially from 1 to 4 inclusive.

As used herein chemical terms (other than IUPAC names for specifically identified compounds) which comprise features which are given in parentheses—such as (alkyl)acrylate, (meth)acrylate and/or (co)polymer—denote that that part in parentheses is optional as the context dictates, so for example the term (meth)acrylate denotes both methacrylate and acrylate.

Unless the context clearly indicates otherwise, as used herein plural forms of the terms herein are to be construed as including the singular form and vice versa.

The term "comprising" as used herein will be understood to mean that the list following is non-exhaustive and may or may not include any other additional suitable items, for example one or more further feature(s), component(s), ingredient(s) and/or substituent(s) as appropriate.

The term 'effective' (for example with reference to the process, uses, products, materials, compounds, monomers, oligomers, polymer precursors and/or polymers of the present invention) will be understood to denote utility in any one or more of the following uses and/or applications: preparation and/or use of a micro-array device and/or component thereof such as a functionalised substrate (preferably for the purpose of chemical analysis and/or synthesis) and/or use of the products and/or results obtained directly and/or indirectly therefrom; and/or any other uses described herein.

Such utility may be direct where the material has the required properties for the aforementioned uses and/or indirect where the material has use as a synthetic intermediate and/or diagnostic tool in preparing materials of direct utility. As used herein the term "suitable" denotes that a functional group is compatible with producing an effective product. The substituents on the repeating unit may be selected to improve the compatibility of the materials with the polymers and/or resins in which they may be formulated and/or incorporated for the aforementioned uses. Thus the size and length of the substituents may be selected to optimise the physical entanglement or interlocation with the resin or they may or may not comprise other reactive entities capable of chemically reacting and/or cross-linking with such other resins.

Certain moieties, species, groups, repeat units, compounds, oligomers, polymers, materials, mixtures, compositions and/or formulations which comprise and/or are used in some or all of the invention as described herein may exist as one or more different forms such as any of those in the following non exhaustive list: stereoisomers (such as enantiomers (e.g. E and/or Z forms), diastereoisomers and/or geometric isomers); tautomers (e.g. keto and/or enol forms), conformers, salts, zwitterions, complexes (such as chelates, clathrates, interstitial compounds, ligand complexes, organometallic complexes, non-stoichiometric complexes, solvates and/or hydrates); isotopically substituted forms, polymeric configurations [such as homo or copolymers, random, graft or block polymers, linear or branched polymers (e.g. star and/or side branched), cross-linked and/or networked polymers, polymers obtainable from di and/or tri-valent repeat units, dendrimers, polymers of different tacticity (e.g. isotactic, syndiotactic or atactic polymers)]; polymorphs (such as interstitial forms, crystalline forms and/or amorphous forms), different phases, solid solutions; combinations thereof and/or mixtures thereof. The present invention comprises and/or uses all such forms which are effective.

One feature of the invention is a coating bearing activated unsaturated moieties therein to bind a DNA and/or other biomolecules onto a substrate. From a practical perspective, there exist many ways to introduce increasing amounts of activated unsaturated moieties in a coating. According to the invention, all processes and methods by which such functions can be made available at the surface of a coating are suitable.

Two methods that are preferred for use as, in and/or with the present invention to obtain coatings containing free activated unsaturated moieties are now described.

In one of these methods the coatings used as, in and/or with the present invention are those obtained and/or obtainable from compositions containing one or more polymer precursor(s) comprising activated unsaturated moiet(ies) as the sole polymerisable group. The polymer precursor(s) may comprise any monomer(s), oligomer(s) and/or prepolymer(s), alone and/or in admixture. These compositions may be cured in any suitable manner which gives the polymers comprising them a sufficient number of free (i.e. reactive) activated unsaturated moiet(ies) to be useful as a functionalised coating.

An alternative method which may be used to prepare coatings used as, in and/or with the present invention comprises polymer precursor(s) comprising functional groups capable of reacting with another functional group of a compound comprising activated unsaturated moiet(ies) (such as (meth) acrylate moiet(ies)). For example, a polymer precursor comprising hydroxy groups can be reacted with acryloyl chloride, or a polymer precursor comprising carboxylic acid groups can be reacted with glycidyl(meth)acrylate. Polymer precursors comprising (meth)acrylate moiet(ies) as the sole chemically polymerisable moiety may also be cured in a manner to give polymers comprising free (meth)acrylate moiet(ies) after polymerisation.

Many different polymers are suitable as polymer precursor(s) and/or polymer coating(s) used as, in and/or with the present invention such as any of the following and/or any mixtures thereof, copolymers thereof and/or combinations thereof in the same species: polyurethane (meth)acrylates, (meth)acrylic (meth)acrylates, polyester (meth)acrylates, epoxy (meth)acrylates, dendritic and/or hyperbranched polyester (meth)acrylates and/or polyurethane acrylates, silicone (meth)acrylates and/or (meth)acrylated amines.

Compositions able to produce suitable polymers (such as those described herein) are any of those well known in the art and preferably belong to the technical field known as radiation curable (radcure) compositions. Effective compositions can exist in any suitable physical and/or form, such as: dispersions, solutions and/or emulsions with for example water and/or organic solvent as the continuous phase; and/or compositions without any water or organic solvent (such as mixtures and/or solid solutions of the polymer precursor(s)). Emulsions may comprise any suitable continuous phase (such as water-in-oil (w/o), oil-in water (o/w) emulsions) and optionally the dispersed phase may also comprise an emulsion (such as water-in-oil-in-water (w/o/w) and/or oil-in-water-in oil (o/w/o) emulsions).

Further suitable polymers and/or compositions comprise those listed in "Surface Coatings Technology," Volume II—Prepolymers and Reactive Diluents—Chemistry & Technology of UV and EB Formulation for Coatings, Inks and Paints, edited by G. Webster and published by Wiley(1997).

Polymerisation may be initiated by any suitable means that can be used to obtain polymer coatings used as, in and/or with the present invention such as those coatings comprising free activated unsaturated moieties. There are two preferred polymerisation initiation methods, thermally and/or by irradiation (such as UV or electron beam radiation). Compositions suitable for thermal polymerisation may comprise a thermal initiator. Polymerisation can also occur under ultraviolet irradiation, and then a photo-initiator is generally present in the composition to aid polymerisation. Electron beam irradiation can also be used.

The quantities of remaining unreacted free activated unsaturated moiet(ies) (such as free (meth)acrylate) may be regulated by the conditions of the polymerisation, such as the temperature, the irradiation dose, the type and quantity of initiator, etc, for example as described in Kinetic Study of Ultrafast Photopolymerization Reactions, C. Decker, B. Elzaouk, D. Decker, J. M. S.-Pure Appl. Chem., A(33), pp. 173-1790 (1996).

Another route which may be used to prepare substrates of the present invention uses coating compositions comprising any polymer precursor(s) (such as monomer(s), oligomer(s) and/or prepolymer(s)) alone or in admixture, at least one of which comprises at least one chemical reactive group(s) capable of polyaddition thereto. Activated unsaturated moieties may also be present in at least one of these polymer precursor(s). Alternatively polymer precursor(s) comprising chemical reactive groups capable of polyaddition thereto may be reacted to form polymer precursor(s) comprising substantially no (meth)acrylate moiet(ies) but which also still comprise reactive group(s) which may then react with other activated unsaturated moiet(ies).

For example, polyurethane polymers (such as those in solvent and/or water dispersions) may be prepared by reacting polyols and poly-isocyanates. Free (meth)acrylate moiet(ies) may thus be incorporated in the polymer as (meth)acrylated alcohols and/or (meth)acrylated polyols, for example by end-capping of isocyanate terminated polymer precursor(s) (which optionally may be fully or partially chain-extended)

and/or as component(s) of the polymer precursor itself (which also optionally may be fully or partially chain-extended).

The same and/or similar method(s) described herein may be used to prepare dendritic and/or hyper-branched hydroxy compounds (such as alcohols and/or polyols) comprising a plurality of (meth)acrylate moiet(ies). The incorporation of such hydroxy compounds in a polyurethanes may produce coatings having a high concentration in free (meth)acrylate moiet(ies).

In an embodiment of the invention, the unsaturated activated moieties of formula I can be directly be bound to a support if $R_4$ represents an alkoxy or halogenosilicon containing substituent.

To this end, a support having hydroxyl groups must be chosen, such as glass or silicon wafer for example. The halosilane group reacts with the hydroxyl groups present on the surface of the support, binding the activated unsaturated moiety directly to the support.

Any suitable substrate of the invention as described herein can be used to make micro-arrays according to the invention. Preferred substrates comprise glass and/or plastics such as polycarbonate (PC), polyester (PE), polyolefins (such as polypropylene (PP)), polyethylene terphthalate (PET), nylon, polystyrene, cycloolefine copolymer (COC) and/or activated cellulose or mixture thereof. Optionally such substrates may be pre-treated (for example by treatment with a high voltage corona discharge) in order to promote adhesion and then may be treated as described herein.

Preferred molecular probes comprise one or more different hydroxy and/or amino group(s); more preferably amino group(s).

Without wishing to be bound by any mechanism, it is believed that the probes comprise chemical groups which readily covalently bond to activated unsaturated moieties, preferably by means of addition reactions. Where the activated unsaturated moiety comprises an unsaturated ester a suitable addition reaction may comprise the well known Michael addition reaction. Preferably such reactions takes place at room temperature during the micro-array manufacturing process. More preferably the reaction occurs between for example an amino comprising species deposited onto the substrate and an unsaturated (hydrocarbylidene) group of an unsaturated ester moiety (such as those comprising (meth) acrylate moiet(ies)) available at the surface of the functionalised substrate.

Preferred organic probes are biomolecules, more preferably DNA, most preferably those containing amino groups. Amino groups are widely widespread reactive groups typically found on biomolecules. In one example of a method of the invention an amine-terminal DNA sequence may be deposited onto a substrate by any suitable method (such as micro-spotting and/or ink jet printing) to react with unsaturated (meth)acrylate moiet(ies) arranged on the substrate in a pre-determined pattern (such as a micro-array).

The main advantages of the present invention include any and/or all of the following:

Any substrate can be treated by a properly formulated coating to be useful for DNA biochips and/or similar applications.

High acrylate densities maybe achieved to yield a corresponding high density of probes per unit area.

The reactivity of acrylate moiet(ies) provides a good balance between the competing requirements of fast immobilisation of the probe on the substrate surface and good storage properties of the functionalised substrate.

There is a reduced number of process steps required to produce a suitable functionalised substrate using the popular delivery technique as compared to an aldehyde functionalised substrate (believed to be the best functionalised substrate previously available), the acrylate functionalised substrates of the invention eliminate the reduction step whilst having comparable if not better reactivity.

The methods used herein are suitable for many materials, so reducing the previous design limitations for micro-arrays and facilitating production of integrated lab-on-chip systems. The functionalised substrates of the invention have good chemical and/or mechanical resistance—especially when radiation curable materials are used. More particularly, when radiation curable materials are used on metallic surfaces, such as silver surfaces found on CD-ROM, it is possible to formulate the coating in order to combine its good binding properties with very good corrosion resistance for the underlying metal layer.

Other aspects and/or preferred features of the present invention not already described herein are given in the claims.

Figure 2:
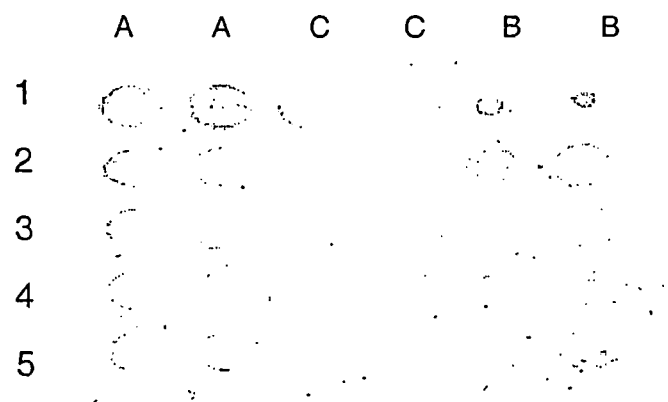

The invention can be illustrated by the following drawings in which:

FIG. 1 is a plot showing DNA grafting efficiency versus free acrylate functionality for a substrate of the invention; and FIG. 2 is picture of micro-array of the invention tested in various fixation and hybridisation experiments as described herein.

The invention will now be illustrated by the following non-limiting examples and tests which are by way of illustration only. The examples comprise two types of formulations (cured thermally or by radiation) which demonstrate and evaluate certain acrylated substrates for use in micro-arrays (such as biochips). In these examples procedures for preparing the substrates are described separately the results used to evaluate the substrates. In the examples herein: NCO values or concentration (also denoted herein as $I_{NCO}$) may be measured using any suitable standard method (such as that described in ASTM D2572-87); hydroxy values or concentration (also denoted herein as $I_{OH}$) may be measured using any suitable standard method (such as that described in E222-73); acid values or concentration (also denoted herein as $I_{H+}$) may be measured using any suitable standard method (such as that described in ASTM D 974-64); and/or free acrylate values or concentration (also denoted herein as $I_{ACR}$) may be measured using any suitable standard method known to those skilled in the art.

Substrate Preparation

Synthesis of Polymer Precursors for Coating

EXAMPLE 1

Synthesis of Hydroxy-Functional Urethane Acrylate

The amount of 444 g of pre-heated 5-isocyanato-1-isocyanatomethyl-1,3,3-trimethylcyclohexane (also known as IPDI and available commercially from Degussa-Huels, Germany) was introduced into a 2 litre four-necked round-bottomed flask equipped with a stirrer, a thermometer, a water cooled condenser and a dropping funnel. The mixture was heated at 45° C. and then 0.37 g of dibutyl tin dilaurate (also known as DBTL and available commercially from Akcros) was added as catalyst. From the dropping funnel 232 g hydroxyethylacrylate and 0.925 g hydroquinone mono methyl ether Were slowly added while the temperature of the reaction mixture was maintained at a maximum of 65° C. The mixture was held at this temperature for one hour until $I_{NCO}$ reached 2.96 meq/g. Then 250 g of di-trimethylolpropane ($I_{OH}$ of 898 mg KOH/g) was added while the reaction was further heated at 65° C. until $I_{NCO}$ dropped below 0.05 meq/g. The oligomer was cooled at 40° C. and diluted with 927 g of butyl acetate to obtain a 50% organic solution of the product urethane acrylate having a viscosity of 135 mPas at 25° C.; $I_{OH}$ of 60 mg KOH/g and 1.078 meq/g of free acrylate ($I_{OH}$ of the solid product was 121 mg KOH/g). This dispersion of urethane acrylate was used directly in the formulations described below.

EXAMPLE 2

Synthesis of Polyol 1,6-Hexanediol (1,144.2 g) and adipic acid (1,135.6 g) (both available commercially from BASF), together with a DBTL catalyst (0.02 g), were mixed in a three litre reaction vessel equipped with an agitator, packed column, condenser, thermometer and inert gas inlet. The reaction vessel was flushed with inert gas and the reactants heated to a temperature of 195° C. to 200° C. while the water produced from the esterification was removed. The reaction was continued for five hours until $I_{H+}$ was 5 mg KOH/g and $I_{OH}$ was 117 mg KOH/g, to obtain as product a polyol with $M_n$ of 1000 and final $I_{OH}$ of 112 mg KOH/g. This polyol was used directly in the formulations described below.

Formulation and Coating of Substrate

Substrates

Functionalised substrates of the invention were prepared from commercial compact-discs (uncoated bare polycarbonate CDs available commercially from ISP, Belgium) which were coated with a topcoat of one of the formulations described herein using a bar coater that deposited a 10 μm thick film of the uncured formulation on the substrate. Other suitable substrates that may also be used are: commercial coated polycarbonate CDs (available commercially from ISP, Belgium) and/or. A4-sized 1 mm thick polycarbonate sheets (available commercially from General Electric, USA). The functionalised substrates of the invention were then tested according to well known standard methods and protocols to demonstrate properties of the micro-arrays of the invention (such as the impact of acrylate concentration on grafting capability—see FIG. 1).

Coating Formulations

Three types of formulations were tested. Two are based on a polymeric backbone (radiation and thermal curing) and one is based on silane chemistry.

Radiation Cured Formulations

UV cured formulations of the invention (Examples 3 & 4) are described below in Table 1. The free acrylate content of the cured coating comes from unreacted unsaturated groups present after UV irradiation. The formulations in Table 1 below were UV-cured by being passed at a speed of 20 m/min, four times under a 80 W/cm medium pressure mercury lamp. All the ingredients in Table 1 except the photo-initiator were obtained from UCB Chemicals under a trade name if indicated in parentheses.

TABLE 1

| | % Weight | |
|---|---|---|
| Ingredient | Example 3 | Example 4 |
| Urethane acrylate (Ebecryl 284) | 40 | 25 |
| Epoxy acrylate (Ebecryl 604) | 40 | 25 |

TABLE 1-continued

| | % Weight | |
|---|---|---|
| Ingredient | Example 3 | Example 4 |
| Hexanediol acrylate | 15 | 45 |
| Benzophenone | 2.5 | 2.5 |
| Photo-initiator (Darocure 1173 from CIBA) | 2.5 | 2.5 |

Thermally Cured Formulations

A wide variety of thermally cured formulations of the invention can be formulated as described herein as the concentration of free acrylate desired in the final substrate can be adjusted by increasing or decreasing the concentration of the hydroxy functional urethane acrylate (such as Example 1) in the formulation. For example the two acrylate groups on the urethane acrylate of Example 1 do not participate in thermally induced polymerisation (cross-linking) and remain available after cross-linking. The formulations in Table 2 below (Examples 5 to 8) were thermally cured in an oven for 3 hours at 60° C. The formulations in Table 2 comprised 9% by weight of the aliphatic polyisocyanate available commercially from Bayer under the trade name Desmodur N3300; (91-X) % of the polyol of Example 2 and X % of the urethane acrylate of Example 1; where the values of X are given in Table 2.

TABLE 2

| Example | X | Free acrylate meq/g |
|---|---|---|
| 5 | 91 | 0.98 |
| 6 | 45 | 0.49 |
| 7 | 23 | 0.24 |
| 8 | 9 | 0.10 |

Silane Based System

Activation of the surface with an activated unsaturated moiety can be performed by a silanization. A glass slide is first cleaned by putting it in a 1:1 methanol:hydrochloric acid solution for 30 min at room temperature. The slides are then rinsed with deionized water until no schlieren lines are observed. After cleaning, the slides are activated. This is accomplished by immersing the slides for 1 hour in a $10^{-3}$ molar anhydrous toluene solution of (3-acryloxypropyl)silane. The samples arethen cleaned by dipping in fresh toluene under vigorous agitation to remove the excess physisorbed molecules and then dried in oven at 120° C. during 10 min.

Preparation of Biochips

Preparation of DNA Capture Probes

The template DNA sequences used for to prepare the nucleotides used as the capture probes in the tests described herein are those of Cytomegalovirus, which were synthesised according to methods and protocols described by Zammateo et al. in Analytic Biochem 253, pp 180-189 (1997). The MIE4 primer so used comprised an amine group at its 5' terminus with an amplicon length of 257 base pairs. DNA sequences were amplified using PCR in a conventional manner and then were separated from unincorporated nucleotides and primers by chromatography on a high pure PCR product purification kit (available commercially from Mannheim, Germany). DNA concentration was measured by its absorbance at 260 nm. The aminated DNA capture probe so obtained was added to a buffered solution to keep a substantial proportion of the amino groups on the probe in their unprotonated state (i.e. as $NH_2$). The buffer solution comprising DNA probes (also known herein as a print buffer) was deposited onto the microarray as described below. The concentration of the DNA probe in each of the different print buffers used herein was 100 nM.

Preparation of Labelled Target DNA

Cytomegalo virus DNA sequences (prepared as described in the aforementioned reference) were also used as the template for target DNA production. The targets DNA had a length of 437 base pairs and was labelled using Biotin-16-dUTP at a DNA to label mole ratio of 1:1 during the PCR amplification. DNA concentration was measured by its absorbence at 260 nm.

Preparing Biochips

DNA capture probes in print buffer were dispensed onto the functionalised resin substrate of the invention using a micro-arrayer (available commercially from WOW, Belgium). Droplets of this print buffer were deposited onto the chips by a suitable method (such as inkjet printing) to yield spots of diameter about 400 µm which were spaced from one another by about 800 µm. The biochips (i.e. the substrate bearing DNA capture probes) was incubated for one hour at 23° C. and subsequently washed once with a 0.2% (by weight) aqueous solution of sodium dodecyl sulphate (also referred to herein as SDS, available commercially from Merck) and then twice with water. The biochip was then incubated for a further three minutes in boiling water to ensure that the single strands of nucleotide sequences were strongly attached the surface.

Hybridisation

A hybridisation solution was prepared comprising the labelled target DNA (prepared as described above) at a concentration of 10 nM in a solution of 0.35M phosphate buffer at pH7 with 4% SDS (such a buffer solution available commercially from AAT, Belgium). The hybridisation solution (70 µl) was added to a hybridisation chamber (available commercially from M J Research, Mass., USA). The chamber was framed onto the micro-array and sealed by a cover slip to bring the solution into contact with the biochip, which was then heated to 50° C. for 2 hours. Afterwards the biochip was washed four times with washing solution (10 mM maleate buffer at pH 7.5 with 0.1% Tween) and then incubated for 45 minutes with a streptavidin-gold conjugate (available commercially from Sigma, Mo., USA). Then the biochip was washed a further five times with the same washing solution and finally incubated for 10 minutes in another incubating solution (that available commercially from AAT, Belgium under the trade name Silver Blue Solution).

Results

Evaluation of the micro-arrays of the invention prepared as described herein was carried out according to well known standard methods and protocols and as described below and shown in FIGS. 1 & 2.

FIG. 1

Functionalised substrates of the invention made from Examples 5 to 8 herein were tested to demonstrate the impact of acrylate concentration on grafting capability. These results are presented in the FIG. 1 herein and illustrate how free acrylate content affects DNA grafting efficiency.

The abscissa of FIG. 1 represents the concentration in units of meq/g of free acrylate functionalities in the coating formulation tested with the resins prepared in Examples 5 to 8 respectively.

The ordinate of FIG. 1 represents the relative grafting efficiency measured as relative DNA surface concentration. This was calculated by comparing the signal intensity measured in each case to that measured for the most concentrated DNA dispersion (200 nM, Example 8) having the highest free acrylate content (0.98 meq/g). Thus the ordinate values are normalised and are dimensionless.

The three plots in FIG. 1 correspond to the test being performed with different concentrations of $NH_2$-DNA probes: 25 nM (bottom line, data denoted by ▲), 50 nM (middle line, data denoted by ◇), and 200 nM (top line, data denoted by ■).

These results clearly indicate that for substrates of the invention the effect of increasing free acrylate concentration is to cause a corresponding increase in the grafting efficiency of the substrate.

FIG. 2

A series of experiments was carried out on a A4-sized 1 mm thick polycarbonate sheet (such as those available commercially from General Electric, USA) which was coated with the formulation of Example 4 herein deposited thereon in various different print buffers. FIG. 2 shows pictures of the micro-array obtained from a colourimetric micro-array reader (available commercially from WOW Belgium) where the print buffer for the probe composition varied in composition and pH as described herein. Each experiment was performed according to standard procedures and as described herein. The results in FIG. 2 were interpreted differently according to the function of each experiment.

In FIG. 2, the rows indicated by numbers denote various print buffers where:

"1" denotes a 0.1M borate buffer of pH 8;

"2" denotes a 0.1M borate buffer of pH 8, with 1M NaCl and 1% SDS,

"3" denotes a 0.1M carbonate buffer of pH 9; and 0.1% SDS;

"4" denotes a 0.1M borate buffer of pH 8; and 0.1% SDS; and

"5" denotes a 0.1M phosphate buffer of pH 7; and 0.1% SDS.

In FIG. 2, the columns indicated by letters denote the function of the experiment where: "A" (×2) denotes fixation control; "B" (×2) denotes negative hybridisation control; and "C" (×2) denotes positive hybridisation control. These experiments are described in more detail below.

DNA sequences derived from the HIV were used for these tests. Primers used to make the HIV derived capture probe correspond to the sequences $NH_2$-GAGGAAGCTGCA-GAAT GGG (SEQ ID NO: 1); and GGTCCTTGTCTTAT-GTCCAGAATGCTG (SEQ ID NO: 2). These amplicons were obtained by amplifying a DNA of 247 bases from "GAG" gene of HIV, by PCR in the conventional manner. The amplicons were then purified on a "High Pure PCR" purification kit and quantified on agarose gel. Capture probes were then deposited as spots on the substrates of the invention at a concentration of 300 nM in different print buffers as described herein.

Fixation Control (A)

This experiment was designed to isolate the fixation step and determine that the capture probe had fixed onto the substrate. Different print buffer solutions were prepared (as described herein) using capture probes that had a biotin label.

A positive response showed on the micro-array as a dark spot and indicated the presence of labelled capture probe.

Positive Hybridisation Control (B)

This experiment was run according to standard micro-array procedures to verify that the whole system worked. A positive response showed as a dark spot on the micro-array and indicated that unlabeled capture probes had attached to the substrate and subsequently been hybridised by their complementary labelled target sequences.

Negative Hybridisation Control. (C)

This experiment was run to detect if there were false positives in experiments A or B. A capture probe corresponding to none of the target sequences present in the hybridisation solution was made up into a print buffer, which was then printed onto the substrate in spots by a suitable means (e.g. an ink-jet printer). Upon completion of the experiment, no hybridisation could have taken place on that spot and thus a dark spot would indicate a problem such as the non-specific binding of the labelled target sequences onto a poorly designed substrate.

Interpretation of Results

One can see in FIG. 2 that, irrespective of the print buffer composition (rows "1" to "5" in Table 2), the fixation control (A) and positive hybridisation control (B) experiments all gave positive results (i.e. a dark spot in the relevant column). Thus the substrate coated with Example 4 did bind aminated DNA capture probes to give properly working micro-arrays (biochips). The negative hybridisation control experiments (C) gave negative results in all cases (i.e. no dark spot, in column C) indicating that the functionalised substrate coated with Example 4 did not give any false positives in this experiment.

Some differences due to the print buffers used can be seen from FIG. 2 as there was some variation in the shape and size of the dark spots where there was a positive result. This is of importance as image analysis software is typically used for reading the results and variations in the spot geometry could alter the readings. Without wishing to be bound by any mechanism it is believed that this variation may be due to differences in surface energy due to the coating. It is believed that this can be compensated for by modifying the print buffer in a manner which does not substantially effect the test to keep the micro-arrays of the invention from producing spots of varying shape.

The results given in FIGS. 1 & 2 herein show the formulations prepared herein (Examples 4 to 8) can be coated on any suitable substrate to produce properly working micro-arrays

The invention claimed is:

1. A process for preparing a substrate (A) having thereon sites reactive with a molecular probe (D) having reactive groups thereon, the process comprising the steps of:

(I) optionally forming a functional coating (B) on the substrate (A);

(II) applying to the optionally coated substrate (A), a binder material (C) comprising at least one reactive site of Formula 1:

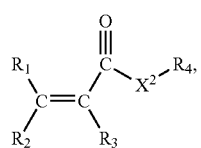

Formula 1 where:

$R_1$, $R_2$ and $R_3$ are each hydrogen;

$R_4$ is an organic group and is capable of linking to optionally coated substrate (A), or where substrate (A) has hydroxyl groups thereon, then $R_4$ is hydrocarbylhalogenosilanyl and is capable of linking directly to substrate (A);

$X^2$ is O; and (III) covalently binding the reactive group of the molecular probe (D) to an activated ethylenically unsaturated double bond of at least one reactive site of Formula 1, where the covalent bond is formed by thermal, non photo-chemical addition.

2. The process according to claim 1, wherein in the binder (C) at least one reactive site of Formula 1 is an acrylate.

3. The process according to claim 1, wherein the substrate (A) is selected from the group consisting of: nylon, polystyrene, glass, silicon wafer, latex, polypropylene, polycarbonate and polyester.

4. The process according to claim 1, wherein the molecular probe (D) is selected from the group consisting of: DNA, RNA, toxins, herbicides, pesticides, carbohydrates, drug targets, antibiotics, cell poisons, steroids, peptides, nucleotides, peptide nucleic acids, binding partners, biotin, proteins and haptens.

5. The process according to claim 1, wherein the reactive group of the molecular probe (D) is an amino group.

6. The process according to claim 1, where in step (I) the coating (B) is formed by polymerization by heat or by irradiation upon the substrate (A).

7. The process according to claim 1, where:

the functional coating (B) comprises at least one polymer precursor selected from the group consisting of polyurethane (meth)acrylates, (meth)acrylic (meth)acrylates, polyester (meth)acrylates, epoxy (meth)acrylates, dendritic polyester (meth)acrylates, hyperbranched polyester (meth)acrylates, polyurethane acrylates, silicone (meth)acrylates and (meth)acrylated amines, wherein the at least one polymer precursor is polymerized on the substrate (A) to leave the coating (B) having unreacted functional groups thereon; and in step (II) the binder (C) comprises additional functional groups reactable with the unreacted functional groups in the coating (B) in addition to the reactive sites of Formula 1, and where the binder (C) reacts with the unreacted functional groups of the coating (B) to leave reactive sites of Formula 1 available to be reacted in step (III) with the reactive groups of the molecular probe (D).

8. The process according to claim 7, wherein, before reaction with the molecular probe (D) in step (III), the coating (B) and the binder (C) formed in steps (I) and (II) are a polymer selected from the group consisting of polyurethane (meth)acrylates, (meth)acrylic (meth)acrylates, polyester (meth)acrylates, epoxy (meth)acrylates, dendritic polyester (meth)acrylates, hyperbranched polyester (meth)acrylates, polyurethane acrylates, silicone (meth)acrylates and (meth)acrylated amines.

9. The process according to claim 1, wherein the substrate (A) bears hydroxyl groups and the reactive groups of the binder (C) are hydrocarbylhalogenosilane acrylate and where in step (II) the hydroxyl groups of the substrate (A) are reacted with the halogenosilane moiety of reactive groups of the binder (C) and where in step (III) the acrylate moiety of the reactive groups of the binder (C) are reacted with the reactive groups of the molecular probe (D).

10. The process according to claim 1, wherein a micro-array is formed and the micro-array is supported on a material selected from the group consisting of membranes, microwells, centrifuge tubes, films and slides.

11. The process according to claim 1, where the linking reaction takes place at room temperature during a process to make a micro-array.

12. The process according to claim 1, where Formula 1 represents an unsaturated ester and the linking reaction is Michael addition.

13. The process according to claim 1, where the linking reaction occurs between an amino comprising species deposited onto the substrate and a hydrocarbylidene group of (meth)acrylate moiet(ies) available at the surface of the functionalized substrate.

14. The process according to claim 1, where Formula 1 is 3-(acryloxypropyl) silane.

15. The process according to claim 1, where in Formula 1: $X^2$ is oxygen; $R_1$, $R_2$ and $R_3$ are H; and $R_4$ is a hydrocarbylhalogenosilane.

16. The process according to claim 1, wherein the at least one non-carbon atom of the organic group is selected from the group consisting of hydrogen, phosphorus, nitrogen, oxygen, silicon and sulphur.

17. The process according to claim 1, wherein $X^2$=O, $R_1$ and $R_2$ are H, $R_3$ is H and $R_4$ is an organic group comprising from 1 to 36 carbon atoms.

18. The process according to claim 1, wherein the organic group is substituted with at least one group selected from the group consisting of carboxy, sulpho, hydroxy, amino, mercapto, cyano, methyl and methoxy.

19. The process according to claim 1, wherein in the binder (C) at least one reactive site of Formula 1 is an acrylate of a $C_{1-4}$alkylsilane.

* * * * *

UNITED STATES PATENT AND TRADEMARK OFFICE
CERTIFICATE OF CORRECTION

PATENT NO. : 8,304,229 B2  Page 1 of 1
APPLICATION NO. : 10/472909
DATED : November 6, 2012
INVENTOR(S) : Luc Lindekens It is certified that error appears in the above-identified patent and that said Letters Patent is hereby corrected as shown below:

Replace the formula found in claim 1 with the following correct formula:

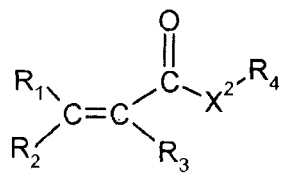

Signed and Sealed this
Twelfth Day of March, 2013

Teresa Stanek Rea
*Acting Director of the United States Patent and Trademark Office*